United States Patent [19]

Girardot et al.

[11] Patent Number: 5,412,830
[45] Date of Patent: May 9, 1995

[54] DUAL TEXTURED IMPLEMENT FOR PERSONAL CLEANSING AND METHOD OF CONSTRUCTION

[75] Inventors: Richard M. Girardot; Eric J. Grosgogeat; Richard G. Bausch, all of Cincinnati, Ohio

[73] Assignee: The Procter & Gamble Company, Cincinnati, Ohio

[21] Appl. No.: 221,430

[22] Filed: Mar. 31, 1994

[51] Int. Cl.6 .............................................. A47L 13/10
[52] U.S. Cl. ...................................... 15/118; 15/209.1
[58] Field of Search ...................... 15/118, 210.1, 208, 15/209.1; 29/419.1, 469

[56]  References Cited

U.S. PATENT DOCUMENTS

| | | | |
|---|---|---|---|
| 1,659,977 | 2/1928 | Kingman | 15/208 |
| 1,963,529 | 6/1934 | Protz | 15/208 |
| 2,151,448 | 3/1939 | Steinberg | 15/208 |
| 2,940,100 | 6/1960 | Grossmeyer | 15/118 |
| 3,169,264 | 2/1965 | Walker | 15/118 |
| 3,241,171 | 4/1965 | Benjamin et al. | 15/118 |
| 3,711,889 | 1/1973 | Jennings | 15/227 |
| 3,772,728 | 11/1973 | Johnson | 15/209 R |
| 3,778,172 | 12/1973 | Myren | 401/7 |
| 3,977,452 | 8/1976 | Wright | 15/209.1 |
| 4,144,612 | 3/1979 | Yamaguchi | 15/208 |
| 4,154,542 | 5/1979 | Rasmason | 401/7 |
| 4,196,490 | 4/1980 | Jonzon | 15/222 |
| 4,206,948 | 6/1980 | Shimizu | 300/21 |
| 4,343,061 | 8/1982 | Hanazono | 15/244 B |
| 4,457,640 | 7/1984 | Anderson | 401/7 |
| 4,462,135 | 7/1984 | Sanford | 15/105 |
| 4,473,611 | 9/1984 | Haq | 15/118 |
| 4,769,022 | 9/1988 | Chang et al. | 604/368 |
| 4,893,371 | 1/1990 | Hartmann | 15/209 B |
| 4,948,585 | 8/1990 | Schlein | 424/40 |
| 4,969,226 | 11/1990 | Seville | 15/244.4 |
| 4,986,681 | 1/1991 | Oliver | 401/7 |
| 4,993,099 | 2/1991 | Emora et al. | 15/118 |
| 5,144,744 | 9/1992 | Campagnoli | 29/446 |
| 5,187,830 | 2/1993 | Giallourakis | 15/244.3 |

FOREIGN PATENT DOCUMENTS 023748 11/1992 European Pat. Off. .
1473147 9/1974 United Kingdom .

OTHER PUBLICATIONS

Copy of an Advertisement for a Commercially Available Product-Exhibit 1.

Primary Examiner—David A. Scherbel
Assistant Examiner—Tony G. Soohoo
Attorney, Agent, or Firm—Ronald W. Kock; Michael E. Hilton

[57]  ABSTRACT

A personal cleansing implement comprises a tubular piece of diamond-mesh scrim, which is stretched to expand the diamond mesh, gathered to form circumferential pleats, heat set in an expanded and pleated condition, and folded into a stack of layers to form a resilient batt. A softer layer of hydrophobic knitted material lies against the top surface of the batt with its outer edge wrapped around the perimeter of the batt and against the bottom surface of the batt. The softer knitted layer is connected to the batt by a connecting means at the outer edge to form a dual textured cleansing implement made of hydrophobic materials and having high open area to enhance rinsing and drying. Thread stitching or thermobonding are the preferred connecting means. A tether loop is connected to the implement for hanging it from a support during drying. The softer knitted layer preferably has at least one aperture therethrough.

20 Claims, 1 Drawing Sheet

DUAL TEXTURED IMPLEMENT FOR PERSONAL CLEANSING AND METHOD OF CONSTRUCTION

FIELD OF THE INVENTION

The present invention relates to hand held implements used for personal cleansing, and more particularly to such implements having both a scrubbing surface made from hydrophobic diamond-mesh scrim, and a sensitive skin surface made from soft, knitted, hydrophobic polymers.

BACKGROUND OF THE INVENTION

A variety of cleansing implements have been used to remove dirt and dead skin from the user's body during bathing or showering. Traditionally, hand held terry washcloths and natural and synthetic sponges have been used. Each of these has one or more significant deficiencies. For example, a sponge has pores which make it difficult to remove dirt from the implement once the dirt is removed from the body. A washcloth often impedes lathering even though lathering is a primary function of a cleansing implement. Some sponges absorb the cleansers that are intended to help remove dirt. Neither sponges nor washcloths can be dried quickly because they become water-logged. As a result they develop unpleasant odors and become a place for breeding bacteria, mold, etc. Also, such implements are typically not suitable for cleaning all body parts. Washcloths are too soft to stimulate and exfoliate skin, and sponges are too rough to cleanse sensitive skin areas.

Some prior art implements have dual textures to provide both soft and harsher surfaces for cleansing different body parts. An example is disclosed in U.S. Pat. No. 3,169,264 to Walker, issued Apr. 19, 1964. It is a hand held multi-purpose wash cloth having one layer made of nylon mesh similar to mosquito netting, and an opposite side layer of cotton dish towel material. The two layers are connected only around their common perimeter by overcast stitching. The cotton layer is intended to be very absorbent, so that like an ordinary washcloth, it is capable of holding liquid and releasing the liquid when squeezed. Therefore, similar to a washcloth, the implement of Walker is slow to dry.

More recently, ball-like structures made of polymer netting have been found in the prior art. An example is disclosed in U.S. Pat. No. 5,144,744 to Campagnoli, issued Sep. 8, 1992. It is hand held and it is made of diamond-mesh polyethylene. Diamond-mesh polyethylene is an extruded scrim material which is commonly found covering vegetables, meat, and poultry.

The implement of Campagnoli is made by stretching multiple tubular pieces of diamond-mesh scrim transversely to their tubular axes and placing each piece over separate support posts. The supported pieces, held in a stretched condition, are arranged either parallel to or at different angles to each other. By tying together the stretched pieces at their centers, and then releasing the pieces from the support posts, each piece springs back toward the tied center to generate a ball-like shape. Prior art ball-like structures similar to Campagnoli's have the stretched pieces of gathered diamond-mesh scrim cinched at their centers, producing a hard dense core, which hinders rinsing and drying. While the surface of Campagnoli's ball-like structure may have high open area, it is difficult to clean the center of the implement for reuse. Furthermore, commercial diamond-mesh scrim is somewhat coarse and therefore harsh to areas of the body having sensitive skin. Commercially available implements of this type are sold by The Body Shop of London, England; and by Bilange of New York, N.Y.

SUMMARY OF THE INVENTION

In practicing the personal cleansing implement of the present invention, an extruded scrim having a diamond-mesh pattern is used to form one body contact surface. The diamond-mesh material is produced in tubular form from a flexible polymer. A second piece of softer material is connected to the diamond-mesh scrim. It is preferably a knitted hydrophobic material having apertures, made from another flexible polymer but with finer strand diameter. The knitted material is therefore softer in a tactile sense than the coarse diamond-mesh scrim material.

In one preferred embodiment of the present invention a personal cleansing implement comprises a piece of diamond-mesh scrim which has been stretched to expand the diamond-mesh. The stretched piece of scrim has also been heat set in the expanded condition, and the expanded piece of scrim has been uniformly folded in a stack of layers to form a hydrophobic batt. The batt has a top surface, a bottom surface and a perimeter. The implement also comprises a softer layer of material connected to the batt. The softer layer has an outer edge and at least one aperture in it. The softer layer is positioned on the top surface of the batt with the outer edge of the softer layer aligned with and adjacent to the perimeter of the batt. The softer layer is connected to the batt at the outer edge by a connecting means to form a dual textured cleansing implement with high open area.

The implement of this embodiment may also comprise a means for hanging it and pleats heat set into the piece of scrim so that the batt is resilient perpendicular to the stack of layers. The softer layer preferably comprises a knitted material.

The outer edge of the softer layer of this embodiment may wrap around the perimeter of the batt to the bottom surface of the batt so that the connecting means connects the outer edge, the batt, and the softer layer placed on the top surface of the batt just inside the perimeter of the batt. This arrangement creates a soft perimeter around the implement. The connecting means may comprise thread stitches through the softer layer and the batt or thermobonding between the softer layer and the batt. The implement may also have connections between the batt and the softer layer internal to the perimeter of the batt so that the stack of layers of the batt experience minimal sliding against each other when the implement is robbed against a body surface.

The result is a resilient implement that may be conveniently gripped. It has a soft knitted side and a coarse diamond-mesh scrim side. The knitted side can be rubbed against sensitive skin without abrasion and the coarse side can be rubbed against less sensitve areas to exfoliate skin. The implement is made of hydrophobic material,, which have a high open area. Construction is such that the central portion of the implement used for cleansing has minimal dense areas, so that the implement may be thoroughly rinsed and quickly dried for reuse.

In a second preferred embodiment of the present invention, a method for making a personal cleansing implement comprises the steps of first cutting a tubular piece diamond-mesh scrim from a source thereof. The tubular piece of scrim has a longitudinal axis. Further steps include stretching the tubular piece of scrim transversely to the longitudinal axis by placing the piece of scrim around a mandrel, and gathering the stretched tubular piece of scrim on the mandrel along the longitudinal axis to form circumferential pleats in the tubular piece of scrim. Another step exposes the stretched tubular piece of scrim having the pleats formed therein to sufficient heat to permanently heat set the tubular piece of scrim in an expanded and pleated condition. Yet additional steps include removing the mandrel from the tubular piece of scrim, extending the expanded and pleated tubular piece of scrim along the longitudinal axis, and folding it into a stack of layers to form a resilient batt. The batt has a top surface and a bottom surface and a perimeter. Still another step of this method involves placing a softer layer of material onto the top surface of the batt. The softer layer has at least one aperture and an outer edge. The outer edge is aligned with and adjacent to the perimeter of the batt. Tha last step includes connecting the outer edge of the softer layer to the perimeter of the batt to form a dual textured cleansing implement with high open area.

The method of this embodiment may further comprise the step of attaching a tether through the personal cleansing implement so that the implement may be hung from a support for drying. Also, the step of connecting the batt to the softer layer may include connections internal to the perimeter of the batt so that the stack of layers of the batt will experience minimal sliding against each other when the implement is rubbed against a body surface. The step of connecting the softer layer to the batt may comprise either stitching thread through the softer layer and the batt or thermobonding the softer layer to the batt.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
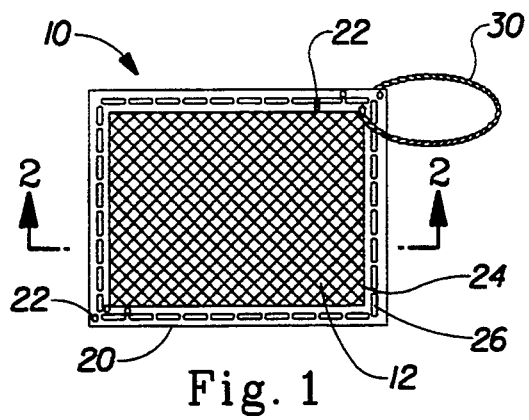
FIG. 1 is a top plan view of a preferred embodiment of the implement for personal cleansing of the present invention, disclosing a rectangular, folded scrim batt covered by an apertured knitted material.
Figure 2:
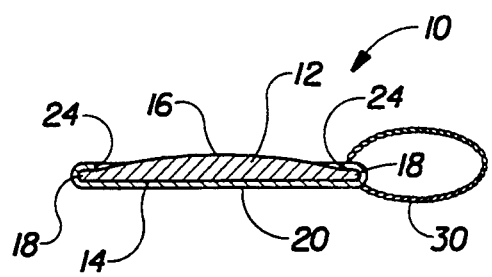
FIG. 2 is a sectioned side elevation view thereof, taken along section line 2—2 of FIG. 1, showing the implement having two sides with different textures.

Referring now to the drawings, and more particularly to FIGS. 1 and 2, there is shown a first preferred embodiment of the present invention, which provides an implement for personal cleansing, and is generally indicated as 10. The implement 10 is made of two primary components. First is a diamond-mesh tubular scrim. Commercial diamond mesh scrim is extruded, chilled and rolled onto spools for storage, shipping, and handling. When personal cleansing implements are made, such material is unwound and cut to desired lengths for assembly. Alternatively, the diamond-mesh scrim could be formed and fed directly to an implement assembly process.

In the present invention a cut length of several feet of diamond mesh scrim is transversely stretched and pleated and then heat set in such in expanded condition. Alternatively, the diamond-mesh scrim could be stretched and heat set when formed and then provided in an expanded condition for implement assembly.

The heat set scrim is extended and then folded several times into a stack of layers to form a resilient batt 12. Batt 12 has a top surface 14 and a bottom surface 16 and a perimeter 18. Batt 12 is connected to a second component which is a softer material layer 20. Softer layer 20 is preferably knitted. Alternatives to knitted layer 20 include nonwoven materials and formed hydrophobic polymer films which are perforated and microtextured for softness. Softer material layer 20 contains at least one aperture 22. It is placed against top surface 14 of batt 12. Apertures in layer 22 enhance lathering when layer 22 is rubbed against the body in the presence of cleanser and water. Preferably there are a plurality of apertures 22. Alternatively, there is one large aperture 22 in softer layer 20, which has edges just inside perimeter 18 of batt 12. In this alternative top surface 14 of batt 12 is exposed through the aperture so that both sides of the implement are essentially the same and the softer layer 20 becomes mererly a border. That is, softer layer 20 would be found on the implement only around perimeter 18 of batt 12.

Figure 8:
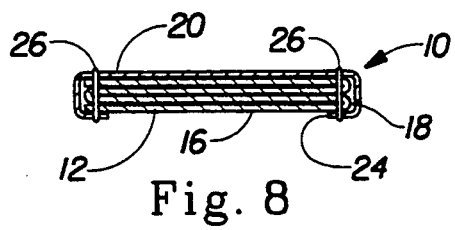
FIG. 8 is a sectioned side elevation view thereof, showing edges of the knitted material wrapped around and stitched to the folded scrim batt.
Figure 9:
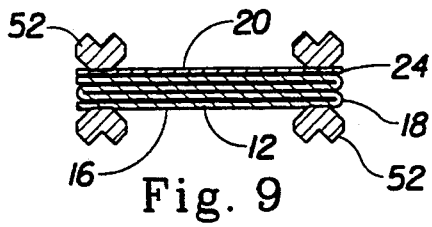
FIG. 9 is a sectioned side elevation view of the embodiment of FIG. 7, showing the outer edge of the softer layer aligned with the perimeter of the batt and thermobonded thereto by sealing dies.

In order to connect resilient and high open area batt 12 to apertured softer layer 20, softer layer 20 has outer edge 24 which is aligned with and adjacent to perimeter 18 of batt 12. Preferably outer edge 24 is wrapped around perimeter 18 and under bottom surface 16 of batt 12, as shown in FIGS. 2 and 8. Alternatively, layer 20 may have outer edge 24 connected to perimeter 18 of batt 12 without being wrapped around perimeter 18, as shown in FIG. 9. FIGS. 1 and 8 show a means for connecting softer layer 20 to batt 12 by stitching with thread 26. Thread 26 is sewn through outer edge 24, through perimeter 18 of batt 12, and through softer layer 20, thereby sandwiching the perimeter 18 of batt 12 between softer layer 20 and its wrapped around outer edge 24. Softer layer 20 may also be heat sealed to batt 12, as shown in FIG. 9 by compressing and heating the perimeter 18 of batt 12 against outer edge 24 of the softer layer 20. However, stitching permits a connection which is less stiff and dense than heat sealing provides.

Implement 10 has a high open area, resilience, and its materials are hydrophobic. This combination provides a significant amount of lather when used with a liquid, gel, or solid form of skin cleanser. The implement is held in one hand. Cleanser is preferably added to the implement rather than to the skin. The cleanser is the rubbed against the skin by the implement in the presence of water, lifting dirt and exfoliated skin into the implement. It is believed that lathering enhances the removal of dirt and exfoliated skin from the surface of the body. The implement of the present design enables substantially more lather and better consistency lather to be developed than is generally possible with a washcloth or sponge. By having a dual texture the user may use the two sides of the same implement to gently clean sensitve skin and to scrub non-sensitive areas of the body.

Once bathing or showering are completed, implement 10 may be quickly rinsed and dried, thereby avoiding the slow drying of washclothes or sponges. The construction of implement 10 provides a center portion which has no hard, dense core, in contrast to implements similar to Campagnoli's, where all pieces of the device are cinched together at the center of the implement. Implement 10 also has no very absorbent layer, in contrast to the implement of Walker. The structure of implement 10 is therefore believed to be more sanitary than such prior art personal cleansing implements.

In order to speed the drying of implement 10, a tether loop 30 is attached so that implement 10 may be hung from a support. Tether 30 is preferably made of a hydrophobic rope material, which is connected near a corner of the implement. The tether loop 30 can be used as a handle or as a hanging means.

In larger size embodiments, batt 12 may be quilted to the softer layer 20. That is, stitching or thermal bonding is used to attach the folded diamond mesh scrim to the softer layer at places internal to the perimeter of the batt. The purpose is to prevent the stacked layers sliding or rolling on each other whenever the implement is rubbed against one's skin. Such quilting is preferably minimized to avoid dense regions within the implement.

Figure 3:
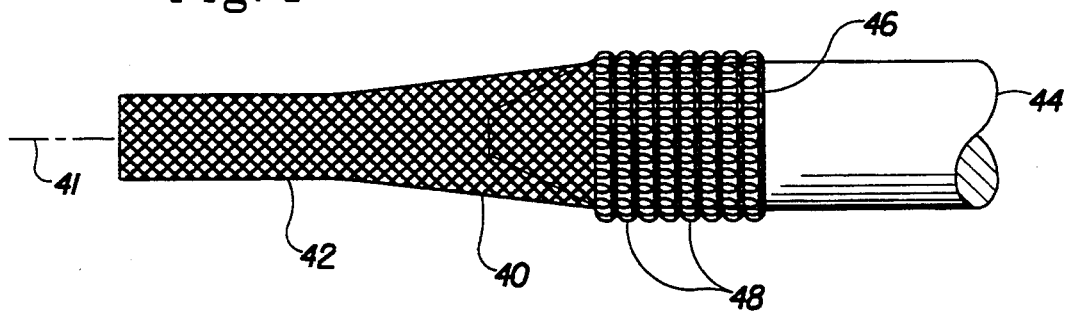
FIG. 3 is a front elevation view of another preferred embodiment of the present invention, disclosing a piece of tubular scrim partially pulled onto a mandrel, the scrim being stretched transversely to its tubular axis and gathered to form circumferential pleats.

FIGS. 3-8 show a preferred method for constructing implement 10. FIG. 3 shows a piece of diamond-mesh polyethylene scrim tubing 40, which initially has an unstretched condition 42 of about 1.0 inch (2.5 cm) diameter and a longitudinal axis 41. Tubing 40 is pulled over the tapered nose of a cylindrical mandrel 44, mandrel 44 having a diameter of about 4.6 inches (11.7 cm), in order to elastically stretch the tubing transverse to longitudinal axis 41. The result of elastic stretching is that diamond-mesh tubing 40, having diamond acute angles of about 5° in condition 42, is transformed to stretched scrim tubing 46, having more open diamond acute angles of about 45°. The scrim tubing 40 is also gathered along its longitudinal axis 41 to form circumferential pleats 48 in stretched scrim tubing 46.

Figure 4:
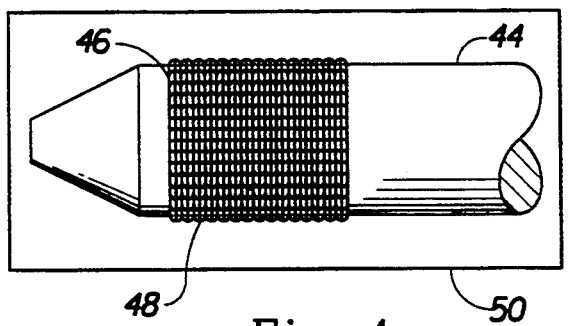
FIG. 4 is a front elevation view thereof, showing the entire piece of tubular scrim gathered on the mandrel and the scrim and mandrel placed in an oven.
Figure 5:
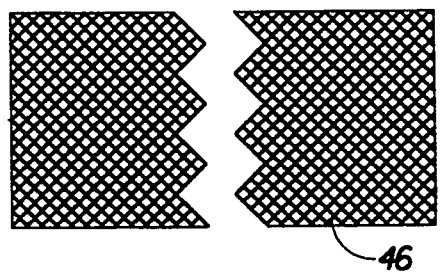
FIG. 5 is a top plan view thereof, showing the mandrel removed and the pleated scrim extended longitudinally for folding.

FIG. 4 shows mandrel 44 and stretched tubing 46 with pleats 48 placed in an oven 50 for about 10 minutes at 140° F. The mandrel is supported in oven 50 by a support not shown so that pleats 48 are not disturbed during heating. The result of heating the transversely stretched scrim tubing, preferably made of polyethylene, is that the transverse stretch is transformed into a permanent heat set condition. Also, pleats 48 are heat set to hold their form as well. When heat set scrim tubing 46 is removed from oven 50 and mandrel 44, and it is extended longitudinally and folded, the undulations of the pleats provide a high loft, 3-dimensional resilient surface to folded scrim tubing 46. Such 3-dimensional effects are not shown in FIGS. 5-8, however. Alternatively, the pleating step could be avoided if a high lofted batt structure were not desired. This would enable using pre-stretched and heat set tubular scrim, which was hereinbefore mentioned as an alternative material source.

Figure 6:
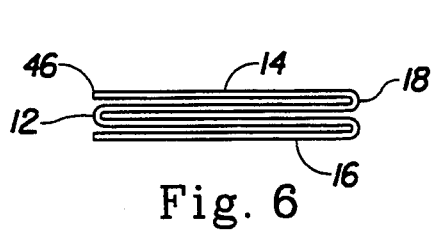
FIG. 6 is a side elevation view thereof, showing the scrim folded into a stack of layers to form a batt.
Figure 7:
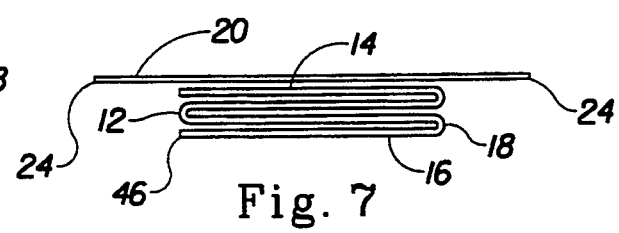
FIG. 7 is a side elevation view thereof, showing the placement of an apertured softer layer onto the top surface of the folded scrim batt.

FIG. 6 shows scrim tubing 46 folded longitudinally into 4 layers of tubing or 8 layers of diamond-mesh to form a substantially rectangular batt 12 which is about 7 inches (17.8 cm) long and 7 inches (17.8 cm) wide, and has top surface 14, bottom surface 16, and perimeter 18. FIG. 7 shows a substantially rectangular piece of apertured knitted material 20 placed against top surface 14 of batt 12. Alternatively, the knitted material may be a piece of non woven or formed film, as noted earlier. The piece of knitted material or layer 20 has dimensions of 7.5 inches (19.1 cm) width and 7.5 inches (19.1 cm) length. Layer 20 has outer edge 24, which may be wrapped around perimeter 18 of batt 12, as shown in FIG. 8. Preferably, batt 12 is connected to layer 20 by thread 26 stitched through outer edge 24 of layer 20, through perimeter 18 of batt 12 and through layer 20 placed against top surface 14 of batt 12. Stitches 26 connect layer 20 to batt 12 all the way around the perimeter 18 of batt 12 to form a soft edge to implement 10. FIG. 8 illustrates the location of stitches 26. FIG. 2 shows a more realistic shape of implement 20 after stitches 26 are pulled tight. Implement 10 then has an overall thickness of about 1.5 inches (3.8 cm). Not shown in FIG. 8, but disclosed in FIGS. 1 and 2, is a tether which is prefereably threaded through an aperture 22 in layer 20 and on through the highly open diamond-mesh scrim of batt 12, preferably located in a corner of implement 10. The tether is tied to form a tether loop 30 which may be hung from a support (not shown) for drying implement 10 after use.

FIG. 9 shows heated sealing dies 52 pressed against bottom surface 16 of batt 12 and against softer layer 20. Dies 52 are heated by a source of heat energy not shown, but which is common in the art. Thermobonding may occur in the form of fusion sealing if the batt and softer layer materials are compatible to fusion sealing. If softer layer 20 and batt 12 are incompatible to fusion sealing, an adhesive layer may be placed between them to achieve thermobonding, as is commonly known in the polymer bonding art.

In a particulary preferred embodiment of the personal cleansing implement of the present invention, diamond-mesh tubular scrim of batt 12 is commercially available from NSW Corporation of Roanoke, Va. It has a specification number PT 589-01, and is described as body mesh having a density of 2.3 grams per foot. Knitted layer 20 is made of nylon and is commercially available from Hancock Fabrics of Cincinnati, Ohio. It has a specification number 3504, and is called Gametime Sports Mesh, having 3/16 inch by ⅛ inch oval apertures, spaced about ¼ inch apart on 45° angles. Basis weight is about 170 grams per yard. Stitches 26 are preferably made of hydrophobic thread made of polyester. Such thread is commercially available from Beachwood, Ltd. of Ohio. It has a specification number 2743 MAA. Tether loop 30 is preferably hydrophobic braided rope made of polypropylene. Such rope is commercially available from Maxi-Cord of Chicago, Ill. It has a specification number W-01, and it is 3.5 mm in diameter.

While particular embodiments of the present invention have been illustrated and described, it will be obvious to those skilled in the art that various changes may be made without departing from the spirit and scope of the invention, and it is intended to cover in the appended claims all such modifications that are within the scope of the invention.

What is claimed is:

1. A personal cleansing implement comprising:
   a) a hydrophobic batt, said batt being a stack of layers of hydrophobic, expanded, heat set, diamond mesh scrim, said batt having a top surface, a bottom surface and a perimeter;
   b) a softer layer of hydrophobic material connected to said batt, said softer layer having at least one aperture therein and an outer edge, said softer layer positioned on said top surface of said batt with said outer edge of said softer layer aligned with and adjacent to said perimeter of said batt, said softer layer connected to said batt at said outer edge by a connecting means to form a dual textured cleansing implement with high open area.

2. The personal cleansing implement of claim 1 further comprising a means for hanging said personal cleansing implement.

3. The personal cleansing implement of claim 1 wherein said softer layer comprises a knitted material.

4. The personal cleansing implement of claim 1 wherein said outer edge of said softer layer wraps around said perimeter of said batt to said bottom surface of said batt so that said connecting means connects said outer edge, said batt, and said softer layer placed on said top surface of said batt just inside said perimeter of said batt in order to create a soft perimeter around said implement.

5. The personal cleansing implement of claim 1 wherein said connecting means comprises thread stitches through said softer layer and said batt.

6. The personal cleansing implement of claim 1 wherein said connecting means comprises thermobonding between said softer layer and said batt.

7. The personal cleansing implement of claim 1 further comprising pleats having been heat set into said piece of scrim so that said batt has high loft and is resilient perpendicular to said stack of layers.

8. The personal cleansing implement of claim 1 further comprising connections between said batt and said softer layer internal to said perimeter of said batt to reduce sliding within said stack of layers when said implement is rubbed against a body surface.

9. A personal cleansing implement comprising:
   a) a hydrophobic batt, said batt being a stack of layers of transversely expanded, heat set, diamond-mesh tubular scrim, said batt having a top surface, a bottom surface and a perimeter;
   b) a softer knitted layer of hydrophobic material connected to said batt, said softer knitted layer having an outer edge and at least one aperture therein, said softer knitted layer positioned on said top surface of said batt with said outer edge of said softer knitted layer aligned with and adjacent to said perimeter of said batt, said softer knitted layer connected to said batt at said outer edge by a connecting means to form a dual textured cleansing implement with high open area.

10. The personal cleansing implement of claim 9 further comprising a means for hanging said personal cleansing implement.

11. The personal cleansing implement of claim 9 wherein said outer edge of said softer knitted layer wraps around said perimeter of said batt to said bottom surface of said batt so that said connecting means connects said outer edge, said batt and said softer knitted layer placed on said top surface of said batt just inside said perimeter of said batt in order to create a soft perimeter around said implement.

12. The personal cleansing implement of claim 9 wherein said connecting means comprises thread stitches through said softer knitted layer and said batt.

13. The personal cleansing implement of claim 9 wherein said connecting means comprises thermobonding between said softer knitted layer and said batt.

14. The personal cleansing implement of claim 9 further comprising pleats heat set into said piece of scrim so that said batt is resilient perpendicular to said stack of layers.

15. The personal cleansing implement of claim 9 further comprising connections between said batt and said softer knitted layer internal to said perimeter of said batt reducing sliding within said stack of layers when said implement is rubbed against a body surface.

16. A method for making a personal cleansing implement comprising the steps of:
   a) cutting a tubular piece diamond-mesh scrim from a source thereof, said tubular piece of scrim having a longitudinal axis;
   b) stretching said tubular piece of scrim transversely to said longitudinal axis by placing said piece of scrim around a mandrel;
   c) gathering said stretched tubular piece of scrim on said mandrel along said longitudinal axis to form circumferential pleats in said tubular piece of scrim;
   d) exposing said stretched tubular piece of scrim having said pleats formed therein to sufficient heat to permanently heat set said tubular piece of scrim in an expanded and pleated condition;
   e) removing said mandrel from said tubular piece of scrim;
   f) extending said expanded and pleated tubular piece of scrim along said longitudinal axis and folding it into a stack of layers to form a resilient batt, said batt having a top surface and a bottom surface and a perimeter;
   g) placing a softer layer of material onto said top surface of said batt, said softer layer having at least one aperture and an outer edge, said outer edge being aligned with and adjacent to said perimeter of said batt;
   h) connecting said outer edge of said softer layer to said perimeter of said batt to form a dual textured cleansing implement with high open area.

17. The method of claim 16 further comprising the step of attaching a tether through said personal cleansing implement so that said implement may be hung from a support for drying.

18. The method of claim 16 further comprising the step of connecting said batt to said softer layer internal to said perimeter of said batt in order to reduce sliding within said stack of layers when said implement is rubbed against a body surface.

19. The method of claim 16 wherein the step of connecting said softer layer to said batt comprises stitching thread through said softer layer and said batt.

20. The method of claim 16 wherein the step of connecting said softer layer to said batt comprises thermobonding said softer layer to said batt.

* * * * *